United States Patent [19]
Canfield

[11] Patent Number: 5,486,201
[45] Date of Patent: Jan. 23, 1996

[54] ACTIVE DISCHARGE OF A COUPLING CAPACITOR IN AN IMPLANTABLE MEDICAL DEVICE

[75] Inventor: Lyle D. Canfield, Lake Hughes, Calif.

[73] Assignee: Pacesetter, Inc., Sylmar, Calif.

[21] Appl. No.: 303,800

[22] Filed: Sep. 12, 1994

[51] Int. Cl.$^6$ .................................................. A61N 1/37
[52] U.S. Cl. ............................................................ 607/13
[58] Field of Search .................................. 607/5, 9, 13

[56] References Cited

U.S. PATENT DOCUMENTS

| | | | |
|---|---|---|---|
| 3,476,117 | 11/1969 | Jonsson | 128/421 |
| 3,885,572 | 5/1975 | Chen | 128/419 P |
| 4,114,627 | 9/1978 | Lewyn et al. | 607/13 |
| 4,406,286 | 9/1983 | Stein | 128/419 PG |
| 4,498,478 | 2/1985 | Bourgeois | 607/13 |
| 4,504,773 | 3/1985 | Suzuki et al. | 320/1 |
| 4,586,507 | 5/1986 | Herscovici | 128/419 PG |
| 4,858,610 | 8/1989 | Callaghan et al. | 128/419 PG |
| 4,991,583 | 2/1991 | Silvian | 607/13 |

*Primary Examiner*—William E. Kamm
*Assistant Examiner*—Kennedy J. Schaetzle
*Attorney, Agent, or Firm*—Malcolm J. Romano; Lisa P. Weinberg

[57] ABSTRACT

An active discharge circuit for use within an implantable medical device, such as a pacemaker, rapidly discharges a coupling capacitor connected between a therapy circuit and body tissue. The active discharge circuit has a switching device, a charge transfer capacitor, and a clock. The clock is coupled to a control input of the switching device and provides a clock signal thereto. In response to the clock signal, the switching device sequentially and repeatedly couples the charge transfer capacitor to a discharge voltage supply so that charge transfers therebetween, and then couples the charge transfer capacitor to the coupling capacitor so that charge transfers therebetween. As the switch oscillates in response to the clock signal, the coupling capacitor is actively discharged.

24 Claims, 7 Drawing Sheets

ACTIVE DISCHARGE OF A COUPLING CAPACITOR IN AN IMPLANTABLE MEDICAL DEVICE

BACKGROUND OF THE INVENTION

Field of the Invention

The present invention relates to implantable medical devices, and more particularly to implantable cardiac pacemakers or pacers that are capable of "pacing" and "sensing" at least one chamber of a heart. Even more particularly, the present invention relates to discharging a coupling capacitor used to couple a pace/sense lead to the cardiac pacemaker so that the pace/sense lead can more quickly be used for "sensing" following delivery of an electrical pulse through the pace/sense lead, i.e., following "pacing."

Generally, a heart stimulator, commonly known as a "pacemaker" or "pacer," uses one or two flexible pace/sense leads having one end (a proximal end) connected to the pacer and the other end (a distal end) connected to electrodes placed in close proximity to the heart. These pace/sense leads are used to stimulate or pace the heart. Also, these pace/sense leads are used to sense the heart activity by picking up electrical signals from the heart.

In order to properly pace or sense, the pacer has to be able to deliver a stimulating pulse to the heart or sense an electrical signal from the heart. This requires that there be an electrical return path for the stimulating pulse or the electrical signal from the heart. If, within a given heart chamber, a unipolar pace/sense lead is used—containing a single conductor—the return path is the conductive body tissues and fluids. The return path is connected to the pacer by connecting the pacer's ground to the pacer's metal enclosure, typically referred to as the pacer "case." The case, in turn, makes contact with the body tissue and/or fluids.

Problematically, the conductive body tissues and fluids are frequently poor conductors. Therefore, a differential voltage may be generated across the return path as the stimulating pulse or electrical signal passes through the body tissues and fluids.

An alternative solution to using a unipolar pace/sense lead in a given heart chamber, or elsewhere within the body, is to use a double lead/electrode, known as a bipolar pace/sense lead. In a bipolar pace/sense lead, a second conductor is generally spiraled over and insulated from a first conductor along the length of the pace/sense lead. At the distal end of the pace/sense lead, one of the conductors is connected to a first electrode, referred to as the "tip" electrode, and the second conductor is connected to a second electrode, referred to as a "ring" electrode. The ring electrode is generally situated 10 to 20 mm from the tip electrode. The tip electrode is typically placed in contact with heart tissue, while the ring electrode is in electrical contact with the blood or other body fluids. Because both body tissue and fluids are conductive, the ring electrode of a bipolar pace/sense lead, in contact with the body fluids, serves as an electrical return for both pacing and sensing. Because the ring electrode is located very close, e.g. 10 to 20 mm from the tip electrode, any differential voltage is eliminated or substantially reduced across the return path.

Thus, pacing or sensing using the pacer case or enclosure as a part of the electrical return path is referred to "unipolar pacing" and "unipolar sensing," whereas pacing or sensing using the pace/sense lead ring electrode and associated pace/sense lead conductor as the electrical return path is referred to as bipolar pacing" and "bipolar sensing."

Typically, a pacer delivers a stimulating current pulse by switchably connecting the electrode tip, through a coupling capacitor, to the negative terminal of a storage capacitor, the positive terminal of the storage capacitor being coupled to the pacer's ground. The voltage stored on this storage capacitor has previously been adjusted or amplified to the desired magnitude by a charging circuit within the pacer. The coupling capacitor is required to prevent DC current from flowing through the tip electrode/body interface. The return path for the pacing pulse is provided by grounding the case or ring electrode, depending on whether unipolar or bipolar pacing is being performed. After delivering the pulse, the coupling capacitor remains charged with a positive charge on its tip electrode side (distal side). The pacer side of the coupling capacitor (proximal side) likewise remains charged. Problematically, this pacer-side charge causes distortions in the sensing of cardiac activity and therefore prevents accurate sensing of cardiac activity through the pace/sense lead. Therefore the pacer-side charge must be removed before such sensing can be accurately achieved.

Heretofore, the pacer-side charge has been removed by connecting it through a discharging switch, and possibly a discharging resistor, to the reference potential. See, e.g. U.S. Pat. Nos. 4,114,627; 4,373,531; 4,858,610; 4,991,583; and 5,170,806. Problematically, this approach to discharging the coupling capacitor provides only limited control over the coupling capacitor's discharge rate, and generally requires the use of at least one resistor, which is problematic if the pacer is constructed on an integrated circuit due to the relatively large space requirement for fabricating a resistor.

Thus, improvements are needed in the discharge circuitry used with a coupling capacitor of a cardiac pacemaker or other implantable stimulator so that the pace/sense lead can more quickly be used for "sensing" following delivery of an electrical pulse, i.e., following "pacing." The present invention advantageously addresses the above and other needs.

SUMMARY OF THE INVENTION

The present invention provides an active discharge circuit that actively discharges a coupling capacitor in an implantable medical device after an electrical pulse has passed through the coupling capacitor from a therapy circuit within the medical device to animal tissue.

A first electrode of the coupling capacitor is coupled to the therapy circuit within the implantable medical device and a second electrode of the coupling capacitor is coupled to the animal tissue. The active discharge circuit includes: (1) switching means; (2) a charge transfer capacitor; (3) a discharge voltage supply; and (4) clock means.

The switching means first couples the charge transfer capacitor between ground and the discharge voltage supply in response to the switching means assuming a first state. In the first state charge is transferred between the charge transfer capacitor and the discharge voltage supply. Next, the switching means couples the charge transfer capacitor between ground and the first electrode of the coupling capacitor in response to the switching means assuming a second state. In the second state charge is transferred between the charge transfer capacitor and the coupling capacitor so as to discharge the coupling capacitor.

The clock means generates an oscillating clock signal that is coupled to the switching means and causes the switching means to sequentially assume the first and second states. Thus, in response to the clock signal the switching means oscillates between the first state and the second state. As a result, the coupling capacitor is actively discharged.

In a further embodiment, the active discharge circuit further includes: (5) a voltage comparator; and (6) a clock-gate circuit. The voltage comparator has a noninverting input, an inverting input and a comparator output. The noninverting input is coupled to the first electrode of the coupling capacitor and the inverting input is connected to ground potential. The comparator output assumes a first voltage when a voltage potential at the first electrode is less than ground potential, and assumes a second voltage when the voltage potential at the first electrode is greater than ground.

The clock-gate circuit has a clock input, a clockgate input and a gate output. The clock input is coupled to the oscillating clock signal, the clock-gate input is coupled to the output of the voltage comparator, and the gate output is coupled to the switching means. In this embodiment, the oscillating clock signal is only coupled to the switching means via the clock-gate circuit. The clock-gate circuit, in turn, passes the oscillating clock signal to the switching means only in response to the comparator's first voltage, and the clock-gate circuit blocks the passage of the oscillating clock signal in response to the comparator's second voltage. As a result, the oscillating clock signal is passed to the switching means, thereby causing the active discharging of the coupling capacitor, only when the voltage potential at the first electrode of the coupling capacitor is less than ground potential; and the oscillating clock signal ceases to be passed to the switching means, thereby ceasing the active discharging of the coupling capacitor, when the voltage potential at the first electrode is greater than ground potential.

The invention can also be characterized as a method for actively discharging a coupling capacitor after an electrical pulse has been passed through the coupling capacitor from a therapy circuit to an animal tissue. The method includes: (a) coupling a charge transfer capacitor to a discharge voltage supply so as to transfer charge between the charge transfer capacitor and the discharge voltage supply; (b) decoupling the charge transfer capacitor from the discharge voltage supply; and (c) coupling, the charge transfer capacitor to the first electrode of the coupling capacitor so as to transfer charge between the charge transfer capacitor and the coupling capacitor. Using this method, the coupling capacitor is at least partially discharged by the transfer of charge between the charge transfer capacitor and the coupling capacitor.

The above method may further include: (d) decoupling the charge transfer capacitor from the first electrode of the coupling capacitor; and (e) repeating steps (a) through (d) so as to discharge the coupling capacitor until a voltage potential at the first electrode reaches approximately a reference potential. As a result, the coupling capacitor is discharged to the reference potential. The reference potential may be ground or any other potential to which the coupling capacitor is to be discharged.

It is therefore a feature of the invention to provide an apparatus and method for discharging a coupling capacitor in an implantable medical device.

It is another feature of the invention to achieve such discharging without the need for resistive elements.

It is a further feature of the invention to perform such discharging using one or more active circuit elements (switching devices).

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1:
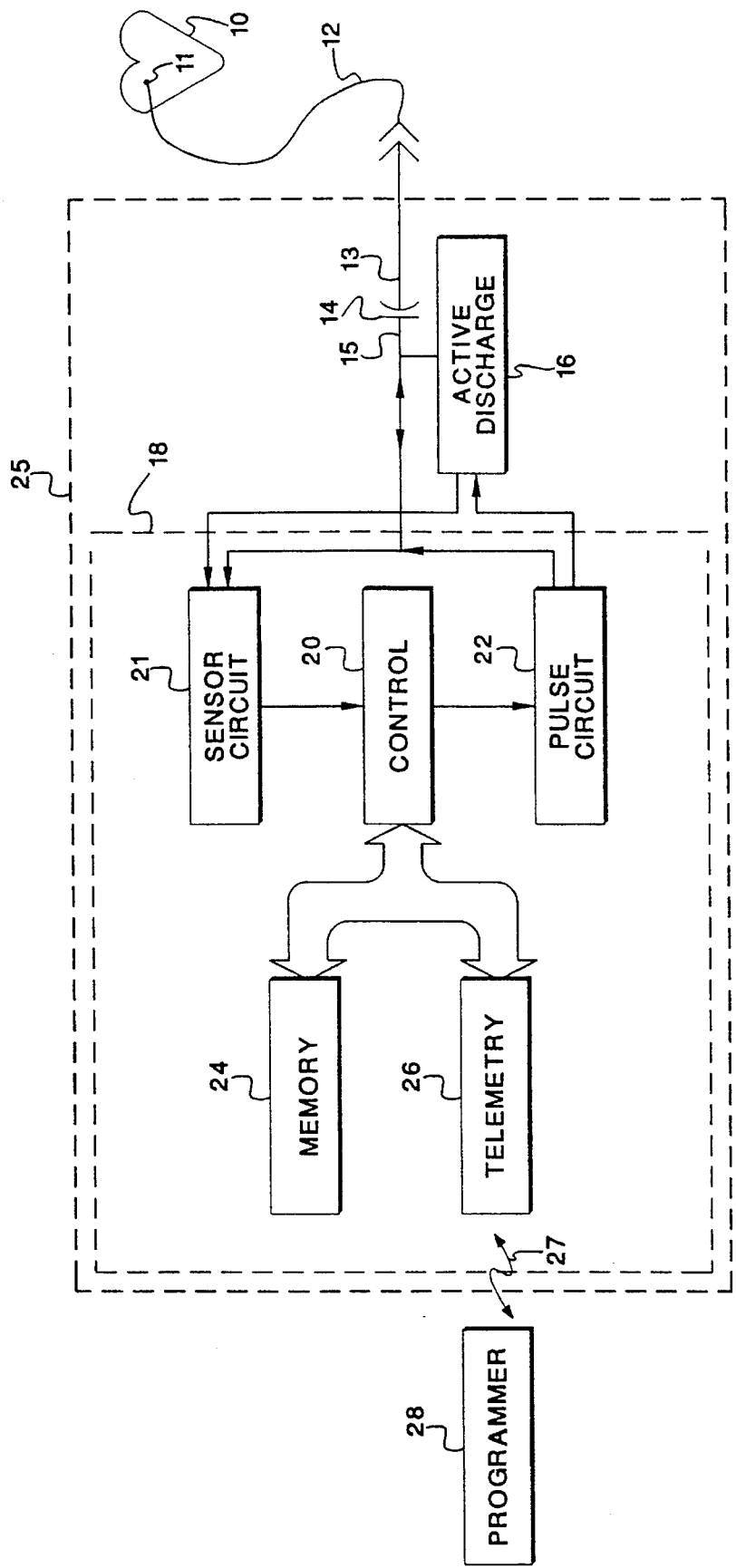
FIG. 1 is a block diagram of an exemplary therapy circuit coupled to an animal heart and to an active discharge circuit of the present invention.

The following description of the presently contemplated best mode of practicing the invention is not to be taken in a limiting sense, but is made merely for the purpose of describing the general principles of the invention. The scope of the invention should be determined with reference to the claims. Referring to FIG. 1, a block diagram is shown of a heart 10, e.g., a human heart, coupled at a tip electrode 11 of a pace/sense lead 12 to a distal (or tip electrode-side) electrode 13 of a coupling capacitor 14. A proximal (or pacer-side) electrode 15 of the coupling capacitor 14 is coupled to an active discharge circuit 16 of the present invention, and to a therapy circuit 18, (e.g., a cardiac pacer). The coupling capacitor 14, the active discharge circuit 16 and the therapy circuit 18 comprise an implantable device 25 that is implanted into a patient and attached to the heart 10 of the patient via the pace/sense lead 12. The pace/sense lead 12 provides electrical communication between the implantable device 25 and the heart 10. The implantable device 25 is housed in an implantable, hermetically sealed housing, as is known in the art of implantable electronic devices.

A sensor circuit 21 is coupled, within the therapy circuit 18, to the proximal electrode 15 of the coupling capacitor 14. The sensor circuit 21 processes an electrical signal that is carried from the heart 10 via the pace/sense lead 12 and the coupling capacitor 14, and generates an output signal in response to the electrical signal. The therapy circuit 18 controls the therapy (typically stimulation pulses) delivered to the heart 10 via the pace/sense lead 12 in response to the output signal.

By way of example, in FIG. 1, the therapy circuit 18 comprises a cardiac pacer. The cardiac pacer includes a control circuit 20, a sensor circuit 21, a pulse generation circuit 22, a memory circuit 24, and a telemetry circuit 26. Representative cardiac pacers are disclosed e.g., in U.S. Pat. Nos. 5,228,438; 5,228,439; and 5,237,992, incorporated herein by reference.

The control circuit 20 receives the output signal from the sensor circuit 21 and, in response thereto, evaluates whether or not optimum therapy is being delivered to the heart 10. If the therapy being delivered is not optimum, the control circuit 20 makes adjustments to the therapy, as required. In determining what is optimum therapy, based on the output signal generated by the sensor circuit 21, the control circuit 20 may also use the memory circuit 24. Various control parameters are stored in the memory circuit 24 by a physician using the telemetry circuit 26. In order to store such parameters, the physician utilizes an external (non-implanted) programmer 28 that is coupled to the memory circuit 24 and/or the control circuit 20 via the telemetry circuit 26 and a suitable communication link 27. Telemetry circuits used for this purpose are known in the art.

In addition to the cardiac pacer, various other therapy circuits 18 may benefit from the active discharge circuit 16 of the present invention, such as other types of cardiac pacers or stimulators, implantable electrical defibrillators, implantable monitoring devices, and the like.

Figure 2:
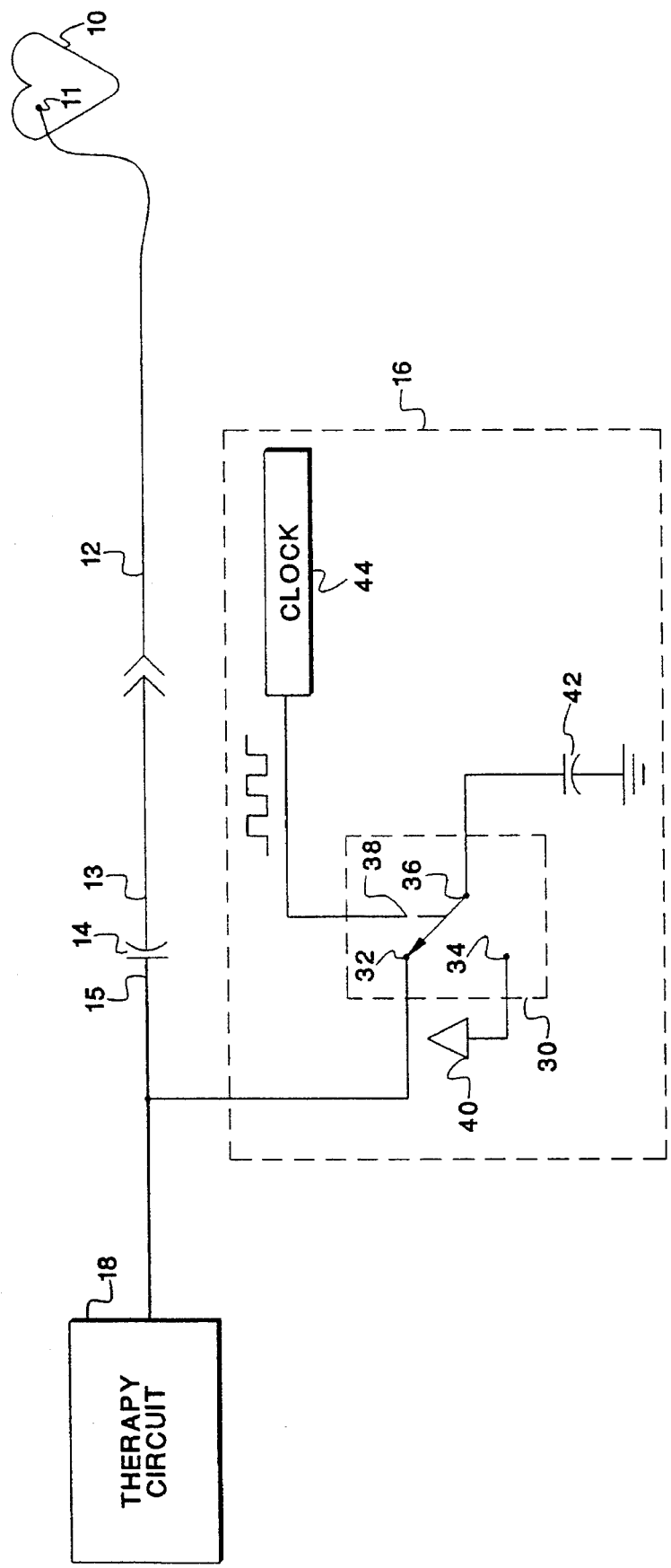
FIG. 2 is a schematic diagram of one embodiment of the active discharge circuit if FIG. 1.

Referring next to FIG. 2, a block diagram is shown of the active discharge circuit 16 of the present invention in combination with the therapy circuit 18, the coupling capacitor 14, the pacer/sense lead 12 and the heart 10. The active discharge circuit 16, and the therapy circuit 18 are coupled to the proximal electrode 15 of the coupling capacitor 14. The distal electrode 13 of the coupling capacitor 14 is coupled to the pace/sense lead 12, and the tip electrode 11 of the pace/sense lead 12 is coupled to the heart 10.

The active discharge circuit 16 includes a switch 30 that has a first pole 32, a second pole 34, a common pole 36, and a control input 38. The first pole 32 is coupled to the proximal electrode 15 of the coupling capacitor 14 and the second pole 34 is coupled to a charge supply 40, e.g., a five-volt power supply. The common pole 36 of the switch 30 is coupled to a charge transfer capacitor 42, which is also coupled to ground, e.g., grounded to a case (or pacer case) of the therapy circuit 18. The control input 38 of the switch 30 is coupled to a clock circuit 44, from which the control input 38 receives a clock signal. In response to the clock signal, the switch 30 causes the common pole 36 to be repeatedly coupled to the first pole 32, then decoupled from the first pole 32, and coupled to the second pole 34, then decoupled from the second pole 34, and coupled back to the first pole 32, and so on. The common pole 36 is never coupled to both the first and second poles 32, 34 simultaneously. As a result, a charge is transferred between the charge supply 40 and the charge transfer capacitor 42 whenever the common pole 36 is coupled to the second pole 34. Similarly, the charge is transferred between the coupling capacitor 14 and the charge transfer capacitor 42 whenever the common pole 36 is coupled to the first pole 32. The rate at which the charge is transferred is proportional to the frequency of the clock signal, which is an oscillating voltage signal. Thus, by controlling the frequency of the clock signal, the rate of discharge of the coupling capacitor 14 can be controlled.

For example, in the event the proximal electrode 15 of the coupling capacitor 14 carries a negative charge after a stimulation pulse from the therapy circuit 18 passes through the coupling capacitor 14, as is typically the case, the charge supply 40 is selected to supply positive charge to the charge transfer capacitor 42, which, in turn, transfers the positive charge to the negatively charged proximal electrode 15 of the coupling capacitor 14 in response to the repeated coupling of the common pole 36 to the first pole 32 and then the second pole 34. In this way, the coupling capacitor 14 is actively discharged after a stimulation pulse (electrical pulse) passes through the coupling capacitor 14. As a result, the pace/sense lead 12, can be used to sense cardiac activity free from distortions that would otherwise be caused by charge on the coupling capacitor 14.

Note generally that before accurate sensing of cardiac activity can be performed, the clock signal must be stopped so that the coupling capacitor 14 does not become too, e.g., positively, charged. Various ways of stopping the clock signal are contemplated within the scope of this invention, with a preferred approach being shown in FIG. 3.

Figure 3:
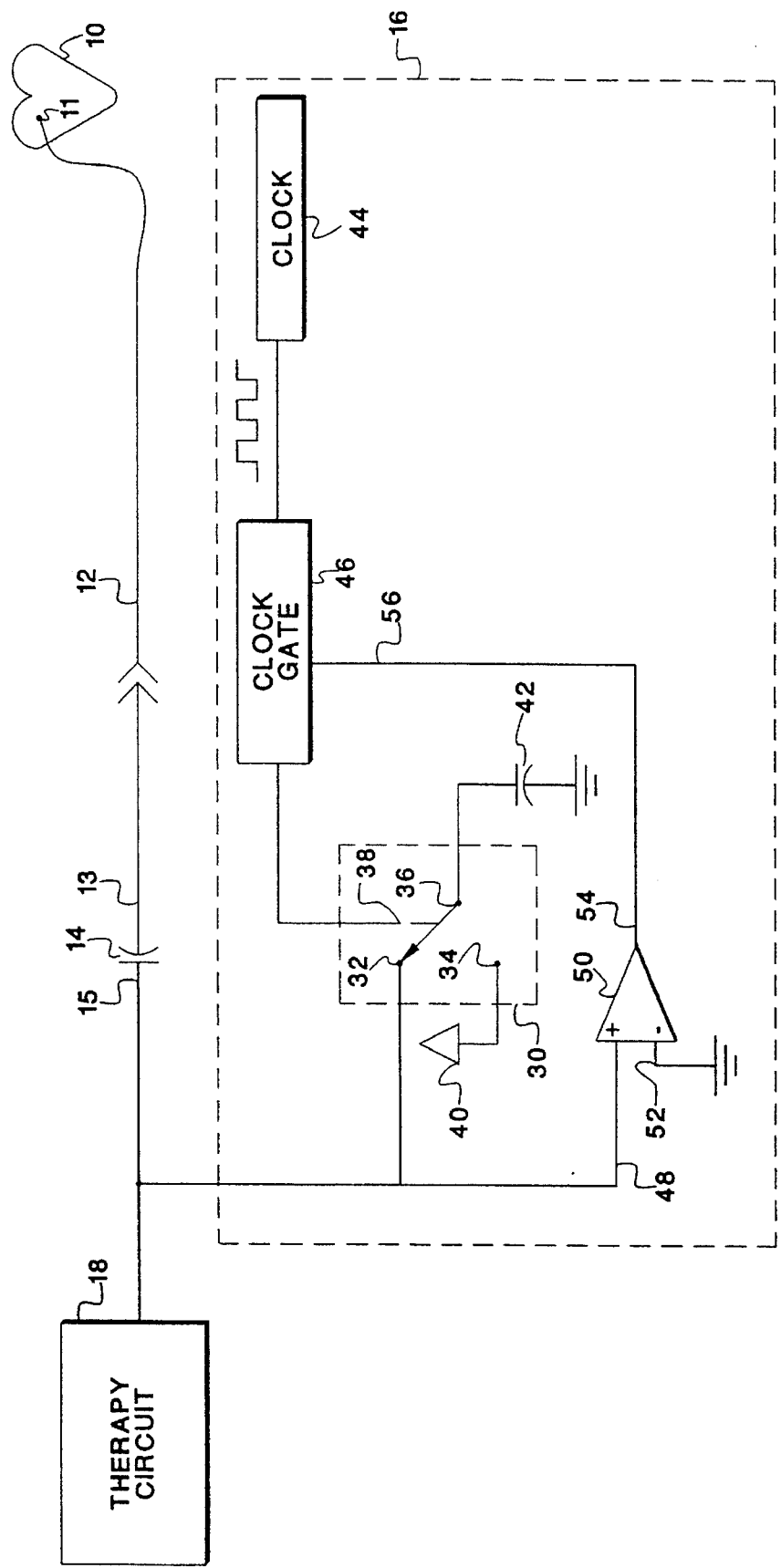
FIG. 3 is a schematic diagram of another embodiment of the active discharge circuit of FIG. 1.

Referring next to FIG. 3, a block diagram is shown of the active discharge circuit 16 of the present invention, wherein the clock signal is selectively coupled through a clock gate circuit 46 to the control input 38 of the switch 30. Also shown, are the active discharge circuit 16, and the therapy circuit 18, which are coupled to the proximal electrode of the coupling capacitor 14. Within the active discharge circuit 16, the proximal electrode 15 of the coupling capacitor 14 is coupled to a non-inverting input 48 of a comparator 50. A reference potential, e.g., case ground, is coupled to an inverting input 52 of the comparator 50, and the output 54 of the comparator is coupled to a clock-gate input 56 of the clock gate circuit 46. As in FIG. 2, the distal electrode 13 of the coupling capacitor 14 is coupled to the pace/sense lead 12, and the tip electrode 11 of the pace/sense lead 12 is coupled to the heart 10.

In operation, a comparator signal is generated at the output 54 of the comparator 50. This comparator signal assumes a first state, e.g., low, in response to the coupling capacitor 14 holding, e.g., a negative voltage (relative to the reference potential). As the coupling capacitor 14 is discharged by the active discharge circuit 16, the voltage across the coupling capacitor 14 decreases in magnitude, and as a result the magnitude of the voltage coupled to the non-inverting input 48 of the comparator 50 decreases (relative to the reference potential that is coupled to the inverting input 52). When the voltage coupled to the non-inverting input 48 reaches approximately zero volts, the comparator signal will assume a second state, e.g., high, in response to which the clock gate circuit 46 will decouple the clock signal from the control input 38 of the switch 30. In response to the decoupling of the clock signal from the switch 30, the switch 30 assumes its, e.g., first state, thereby coupling the common pole 36 to the first pole 34. The clock gate circuit 46 will continue to decouple the clock signal from the switch 30 so long as the coupling capacitor 14 remains discharged, i.e., generally until the next stimulation pulse is delivered to the heart 10 by the therapy circuit 18, at which time a voltage of non-zero magnitude will again develop across the coupling capacitor 14 and be coupled to the non-inverting input 48 of the comparator 50. In response to the voltage of non-zero magnitude, the comparator signal will again assume the first state, and the coupling capacitor 14 will again begin actively discharging.

In addition to the comparator 50 and the clock gate circuit 46, the active discharge circuit 16 includes the switch 30, the charge transfer capacitor 42 and the clock circuit 44, as described above.

Figure 4:
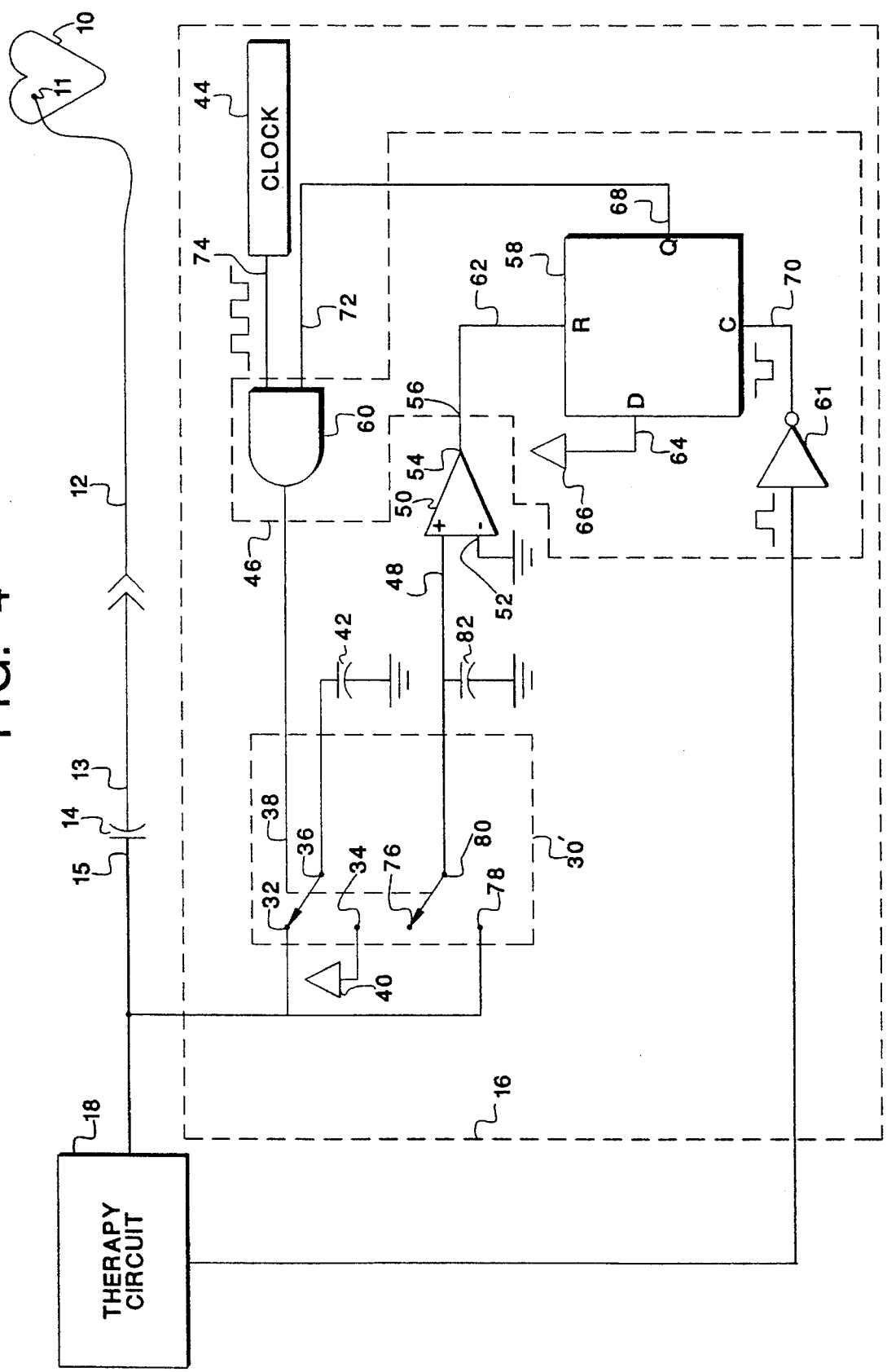
FIG. 4 is a schematic diagram of a further embodiment of the active discharge circuit of FIG. 1.

Referring next to FIG. 4, a block diagram is shown of the active discharge circuit 16 of the present invention, wherein the clock signal is selectively coupled through the clock gate circuit 46 to the control input 38 of a switch 30. The clock gate circuit 46 consists of a latching device 58, e.g., a D-latch, a T-latch, an S-R-latch, or a J-K-latch, and a logic gate 60, e.g., an AND gate or a NOR gate. The embodiment of FIG. 4, also includes an inverter 61.

Also shown, are the active discharge circuit 16, and the therapy circuit 18, which are coupled to the proximal electrode of the coupling capacitor 14. Within the active discharge circuit 16, the proximal electrode 15 of the coupling capacitor 14 is coupled to the non-inverting input 48 of the comparator 50. The reference potential, e.g., ground, is coupled to an inverting input 52 of the comparator 50, and an output 54 of the comparator is coupled to the clock-gate input 56 of the clock gate circuit 46. The clock gate input 56 is coupled to a reset input 62 of the latching device 58 within the clock gate circuit 46. As in FIG. 2, the distal electrode 13 of the coupling capacitor 14 is coupled to the pace/sense lead 12, and the tip electrode 11 of the pace/sense lead 12 is coupled to the heart 10. A data input 64 of the latching device 58 is coupled to an enabling voltage 66. A pulse signal (or trigger signal), indicative of the delivery of the stimulation pulse, is coupled from the therapy circuit 18, through the inverter 61 to a clock input 70 of the latching device 58. The trigger signal, for example, may normally assume a low state while the stimulation pulse is not being delivered, and may assume a high state while the stimulation pulse is being delivered. When the stimulation pulse is delivered, therefore, the trigger signal assumes a high state, and the high state is inverted (to the low state), by the inverter 61. Similarly, when the stimulation pulse ceases to be delivered, the trigger signal will present a low state to high state transition, or rising edge, to the clock input 70 of the latching device 58, (i.e., a high to low transition, or falling edge, having been inverted by the inverter 61). This rising edge causes the latching device 58 to read the enabling voltage from the data input 64, and causes a latch signal that is present at an output 68 of the latching device 58 to assume an enabled state. The latch signal remains in the enabled state until the comparator signal assumes its second state, thereby resetting the latching device 58 via the reset input 62, causing the latch signal to assume a disabled state. The latch signal remains in the disabled state until the rising edge of the trigger signal (i.e., the falling edge having been inverted) is again applied to the clock input 70 of the latching device 58, as described above.

The output 68 of the latching device 58 is coupled to a first input 72 of the gate device 60, and a second input 74 of the gate device 60 serves as the clock input of the clock-gate device 46, and is coupled to the clock circuit 44. When the latch signal is in the enabled state, the gate device 60 couples the clock signal from the clock circuit 44 through the gate device 60 to the control input of the switch 30'. On the other hand, when the latch signal is in the disabled state, the gate device decouples the clock signal from the switch 30', thereby causing the switch 30' to assume its first state, as described above in the description of the switch 30.

Another aspect of the embodiment of FIG. 4 is that the switch 30' has two first poles 32, 76, two second poles 34, 78, two common poles 36, 80 and the control pole 38 (or control input) described above. The switch 30' sequentially assumes its first and second states in response to the clock signal being coupled to the switch 30' by the clock-gate circuit 46, and assumes, e.g., its first state in response to the clock signal being decoupled from the clock gate circuit 46. In its first state, the switch 30' couples the common poles 36, 80 to the first poles 32, 76, each respectively, and in the second state the switch 30' couples each of the common poles 36, 80 to respective second poles 34, 78. A first set of the first, second, and common poles 32, 34, 36 corresponds to respective first, second, and common poles 32, 34, 36 described in conjunction with FIG. 2 and functions in the manner described above. The first pole 76 of a second set of first second and common poles 76, 78, 80 is an open circuit. The second pole 78 of the second set is coupled to the proximal electrode 15 of the coupling capacitor 14, and the common pole 80 of the second set is coupled to the non-inverting input 48 of the comparator 50. A charge holding capacitor 82 is coupled between the non-inverting input 48 and the reference potential. Thus, when the switch 31' assumes its first state, the charge holding capacitor 82 and the non-inverting input 48 are decoupled from the first electrode 15 of the coupling capacitor 14. Conversely, when the switch 31' is in its second state, the charge holding capacitor 82 and the non-inverting input 48 are coupled to the first electrode 15 of the coupling capacitor 14. As a result, charge is transferred between the coupling capacitor 14 and the charge holding capacitor 82 only when the switch 30' is in its second state, and, as explained above, charge is transferred between the coupling capacitor 14 and the charge transfer capacitor 42 only when the switch 30' is in its first state. The charge holding capacitor 82 holds approximately the same voltage as is held by the coupling capacitor 14, so long as the switch 31' is oscillating between its first and second states.

Differences in voltage held by the charge holding capacitor 82 and the coupling capacitor 14 are attributable to two sources. The first is the decoupling of the charge holding capacitor 82 when the switch 31' is in its first state. This source of error is generally very small, and prudent selection of a clock frequency for the clock circuit 44, and capacitance values for the charge holding capacitor 82 and the coupling capacitor 14 can be used to minimize such error. In contrast, the second source of error is more problematic, i.e., differential polarization between the reference potential, e.g., pacer case electrode, and the tip electrode 11 of the pace/sense lead 12. One solution to this potential source of error is shown in FIG. 6., described hereinbelow.

Figure 5:
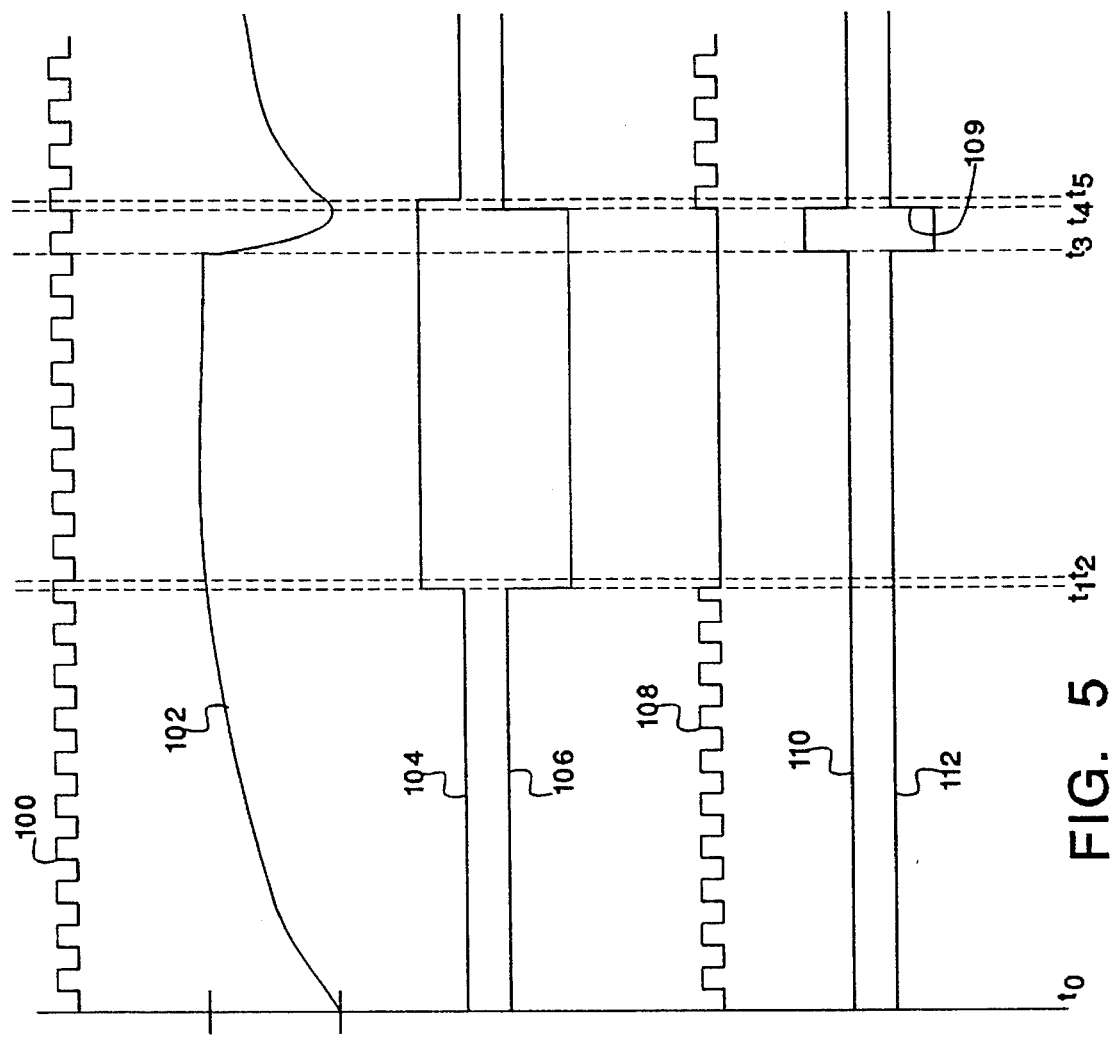
FIG. 5 is a timing diagram illustrating various signals that are utilized within the active discharge circuit embodiment of FIG.4.

Referring next to FIG. 5, a timing diagram is shown of several exemplary timing waveforms. The clock signal 100 that is generated by the clock circuit, and the voltage across the coupling capacitor 102 are shown. At time $t_0$ the coupling capacitor begins to discharge from, e.g., a negative voltage—as is typically the case after the therapy unit delivers a pulse—to the reference potential. In response to the coupling capacitor voltage reaching or coming very near to the reference potential at time $t_1$, the comparator signal 104 transitions from a first state to a second state. In response to this transition the latch signal 106 (at the output of the latch device) assumes the disabled state. The disabled state of the latch signal causes the clock gate circuit to decouple the clock signal from the control input of the switch 30'. Thus the signal 108 at the clock output of the clock-gate circuit is no longer the clock signal 100. Note that the cessation of the clock signal at the clock output of the clock-gate circuit, in this embodiment, need not coincide with the end of a clock cycle or period, e.g., at time $t_2$.

The latch signal 106 remains in its disabled state until such time as the rising edge 109 of the pulse signal 110, after being inverted 112, is received at time $t_4$ into the clock input of the latching device. The receiving of the rising edge causes the latching device to read the enabling voltage at the data input of the latching device. This causes the output of the latching device to again assume its enabled state, and causes the clock signal to again be passed through the gate device to the switch 31'. Shortly after the enabled state is again assumed, e.g., at time $t_5$, the comparator signal 104 again assumes its first state (until such time as the voltage across the coupling capacitor again reaches approximately the reference voltage).

Figure 6:
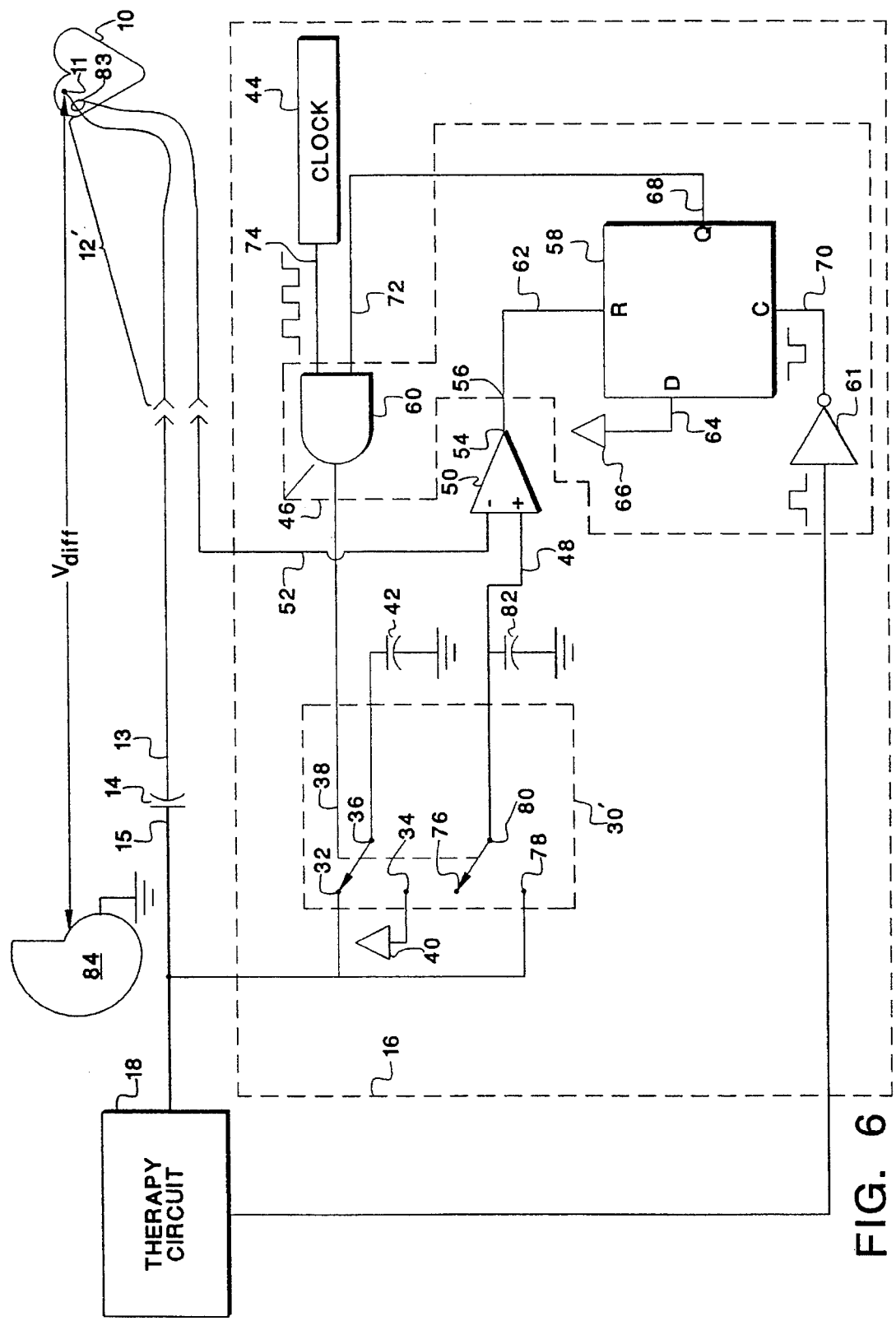
FIG. 6 is a schematic diagram of an alternative embodiment of the active discharge circuit of FIG. 4.

Referring first to FIG. 6, a block diagram is shown of an alternative embodiment of the active discharge circuit 16 of the present invention. The embodiment of FIG. 6 is identical to the embodiment of FIG. 5, except in than the inverting input 52 of the comparator 50 is not coupled to ground 84, i.e., is not coupled to the pacer case 84. Instead, the inverting input 52 is coupled to the ring electrode 83 of a bipolar lead 12'. As a result, the magnitude of the voltage across the coupling capacitor 14 is more accurately sensed. This is because the differential voltage $V_{diff}$ between the pacer case 84, i.e., ground, and the tip electrode 11 is substantially eliminated by providing an electrical return path through the ring electrode of the bipolar lead 12'.

Because the inverting input 52 of the comparator 50 is coupled to the ring electrode 83, because the non-inverting input 48 is repeatedly coupled to the proximal electrode 15 of the coupling capacitor, and because the distal electrode 13 of the coupling capacitor 14 is coupled to the tip electrode 11, the only voltage difference between the voltage across the coupling capacitor 14 and the voltage between the inverting and non-inverting inputs 52,48 of the comparator 50 is the potential difference, if any, between the tip and ring electrodes 11,83. This potential difference, however, can reasonably be assumed to be near zero, because the tip and ring electrodes 11,83 are in close proximity to each other. Thus, the voltage, and therefore the charge, on the coupling capacitor 14 can be more accurately determined, and as a result, the charge can more dependably be removed from the coupling capacitor 14.

Figure 7:
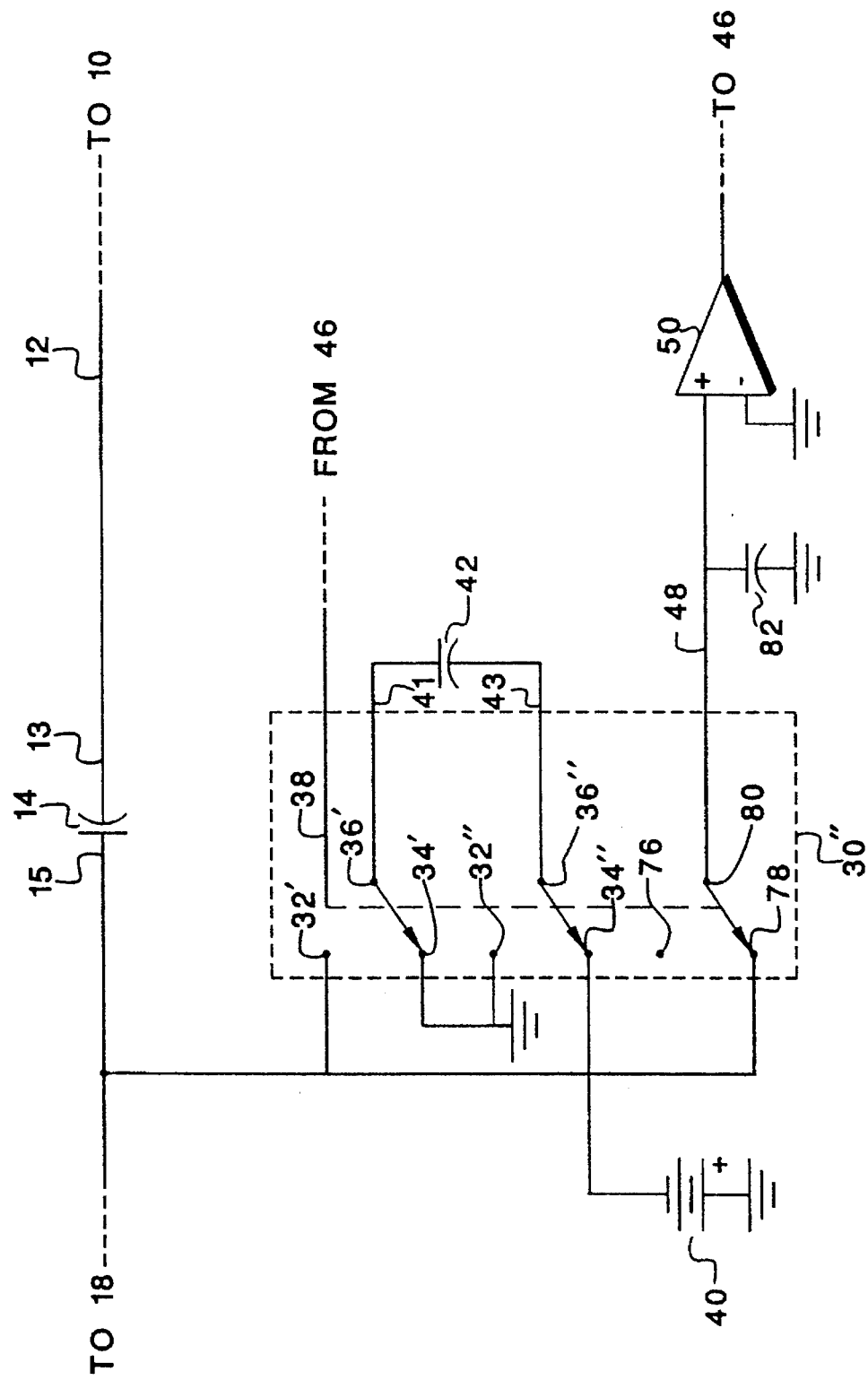
FIG. 7 is a partial schematic diagram of a further embodiment of the active discharge circuits of FIGS. 4 and 6.

Referring next to FIG. 7, a partial schematic diagram is shown of a further embodiment of the active discharge circuit. The therapy circuit 10, the heart 10, the clock gate circuit 46, and the clock circuit 44 are not shown. It should be understood however, that the teachings of FIG. 7 could easily be applied to the active discharge circuits of FIGS. 1, 2, 3, 4 and 6 by one skilled in the art.

In FIG. 7, a switch 30" is shown having first, second and third common poles 36', 36", 80, first, second and third first poles 32', 32", 76, and first, second and third second poles 34', 34", 78. In a first state the switch 30" couples the first poles 32', 32", 76 to the common poles 36', 36", 80, and in a second state the switch 30" couples the second poles 34', 34", 78 to the common poles 36', 36", 80. The switch 30" is controlled to assume the first and second states by a control input 38, and in operation oscillates between the first and second states, i.e., between coupling the common poles 36', 36", 80 to the first and second poles 32', 32", 76 and 34', 34", 78, respectively, in response to the clock signal (described above) being coupled to the control input 38. The switch 30" assumes the second state (as shown) when the clock signal is not applied to the control input 38.

The first common pole 36' is coupled to a first electrode 41 of the charge transfer capacitor 42, and the second common pole 36" is coupled to a second electrode 43 of the charge transfer capacitor 42. The third common pole 80 is coupled to the charge holding capacitor 82, which is described above. The first first pole 32' is coupled to the proximal electrode 15 of the coupling capacitor 14, as is the third second pole 78. The first second pole 34' is coupled to ground, as is the second first pole 32". The second second pole 34" is coupled to the discharge power supply 40, and the third first pole 76 is an open circuit.

In practice when the clock signal is applied to the control input 38, the charge transfer capacitor 42 is first coupled at its first electrode 41 to ground and at its second electrode 43 to the discharge power supply 40. Then, in response to the clock signal, the charge transfer capacitor 42 is coupled at its first electrode 41 to the proximal electrode 15 of the coupling capacitor 14, and at its second electrode 43 to ground. The charge holding capacitor 82 is coupled and then decoupled from the proximal electrode 15 of the coupling capacitor 14, as described hereinabove.

In this way, the coupling capacitor 14 is actively discharged such that the pace/sense lead 12 can more quickly be utilized for sensing, after the delivery of an electrical pulse (stimulation pulse) to the heart by the therapy circuit, i.e., pacing.

While the invention herein disclosed has been described by means of specific embodiments and applications thereof, numerous modifications and variations could be made thereto by those skilled in the art without departing from the scope of the invention set forth in the claims.

What is claimed is:

1. In an implantable medical device, including a therapy circuit, a coupling capacitor coupled to the therapy circuit, and an active discharge circuit for actively discharging the coupling capacitor after an electrical pulse has been passed through the coupling capacitor from the therapy circuit to animal tissue, the coupling capacitor having first and second electrodes, wherein the first electrode of the coupling capacitor is coupled to the therapy circuit and wherein the second electrode of the coupling capacitor may be coupled to animal tissue, the active discharge circuit including:

a charge supply;

a charge transfer capacitor;

switching means for coupling the charge transfer capacitor between ground potential and the charge supply in response to the switching means assuming a first state, wherein charge is transferred between the charge transfer capacitor and the charge supply, and for coupling the charge transfer capacitor between ground potential and the first electrode of the coupling capacitor in response to the switching means assuming a second state, wherein charge is transferred between the charge transfer capacitor and the coupling capacitor so as to discharge the coupling capacitor; and clock means for generating an oscillating clock signal and for causing the switching means to sequentially assume the first state and the second state, the clock signal being coupled to the switching means, whereby the switching means oscillates between the first state and the second state;

whereby the coupling capacitor is actively discharged in response to the oscillating of the first switching device between the first and second states.

2. The active discharge circuit of claim 1, wherein the switching means includes:

a first switching device having a first pole, a second pole, a common pole and a control input, wherein the first switching device is capable of being coupled at its first pole to the first electrode of the coupling capacitor, coupled at its second pole to the charge supply, and coupled at its control input to the clock means;

the charge transfer capacitor being coupled between a ground potential and the common pole of the first switching device such that in a first state the first switching device couples the charge transfer capacitor to the charge supply, whereby charge is capable of being transferred between the charge supply and the charge transfer capacitor, and in a second state the first switching device electrically interconnects the charge transfer capacitor to the first electrode of the coupling capacitor, whereby charge is transferred between the charge transfer capacitor and the coupling capacitor.

3. The active discharge circuit of claim 1, wherein the switching means includes:

a first switching device having a first pole, a second pole, a common pole and a control input, wherein the first switching device is coupled at its first pole to the first electrode of the coupling capacitor, coupled at its second pole to ground potential, and coupled at its control input to the clock means;

a second switching device having a first pole, a second pole, a common pole and a control input, wherein the second switching device is coupled at its first pole to ground potential, coupled at its second pole to the charge supply, and coupled at its control input to the clock means;

the charge transfer capacitor being coupled between the common pole of the first switching device and the common pole of the second switching device such that in a first state the first and second switching devices couple the charge transfer capacitor to the charge supply, whereby charge is capable of being transferred between the charge supply and the charge transfer capacitor, and in a second state the first and second switching devices electrically interconnects the charge transfer capacitor to the first electrode of the coupling capacitor, whereby charge is capable of being transferred between the charge transfer capacitor and the coupling capacitor.

4. The active discharge device of claim 1, including:

a voltage comparator having a noninverting input, an inverting input and a comparator output, wherein the noninverting input is capable of being coupled to the first electrode of the coupling capacitor and the inverting input is coupled to a reference voltage such that the comparator output assumes a first voltage when a voltage potential at the first electrode is less than the reference potential, and the comparator output assumes a second voltage when the voltage potential at the first electrode is greater than the reference potential; and a clock-gate circuit having an clock input, a clock-gate input and a clock-gate output, wherein the clock input is coupled to the oscillating clock signal, the clock-gate input is coupled to the comparator output, and the clock-gate output is coupled to the switching means for causing the switching means to assume the first and the second states, wherein the oscillating clock signal is only coupled to the switching means at the control input via the clock-gate circuit, and the clock-gate circuit passes the oscillating clock signal to the switching means in response to the first voltage, and blocks the passage of the oscillating clock signal to the switching means in response to the second voltage, whereby the oscillating clock signal is passed to the switching means in response to the voltage potential at the first electrode being less than the reference potential, thereby causing the active discharging of the coupling capacitor, and whereby the oscillating clock signal ceases to be passed to the switching means in response to the voltage potential at the first electrode being greater than the reference potential, thereby ceasing the active discharging of the coupling capacitor.

5. The active discharge device of claim 4, including:

a trigger input of the clock-gate circuit that is capable of being coupled to the therapy circuit, wherein the clock-gate circuit passes the oscillating clock signal to the switching means only in response to both the first voltage, and the completion of the delivery of the electrical pulse to the animal tissue, whereby the passage of the oscillating clock signal to the switching means commences only after the delivery of the electrical pulse, thereby commencing the discharging of the coupling capacitor only after the delivery of the electrical pulse.

6. The active discharge device of claim 5, wherein the clock-gate circuit comprises:

a latching device having a reset input, a data input, the trigger input and a latched output, wherein the reset input is the clock-gate input and is coupled to the comparator output, the data input is coupled to an enable voltage supply, and the trigger input is coupled to the therapy circuit, wherein the latched output assumes an enabled state in the event both the comparator output assumes the first voltage and the trigger signal is generated by the therapy circuit, and wherein the latched output assumes a disabled state in the event the comparator output assumes the second voltage; and a gate device with a first input, a second input and a gate device output, wherein the first input is coupled to the latched output, the second input is the clock input and is coupled to the oscillating clock, and the gate device output is coupled to the switching means, wherein the oscillating clock signal is passed through the gate device output to the control input of the switching means in the event the latched output assumes the enabled state, and is not passed to the control input of the switching means in the event the latched output assumes the disabled state, wherein the switching means assumes the first state when the oscillating clock signal is not passed to the switching means, whereby the switching means is controlled to oscillate between the first and second states in response to the passage of the oscillating clock signal through the gate device and whereby the switching means is controlled to assume the first state in response to the non-passage of the oscillating clock signal through the gate device;

whereby the coupling capacitor is actively discharged in response to the passage of the oscillating clock signal, and whereby the coupling capacitor is not actively discharged in response to the non-passage of the oscillating clock signal.

7. The active discharge device of claim 6, including:

a switching device having a first pole, a common pole, and a control input, wherein the switching device is coupled at its first pole to the first electrode of the coupling capacitor and at its common pole to the noninverting input of the voltage comparator such that the noninverting input of the voltage comparator is only coupled to the first electrode of the coupling capacitor via the switching device, and wherein the switching device is coupled at its control input to the gate output such that the switching device assumes a first state whenever the switching means assumes its first state, and the switching device assumes its second state whenever the switching means assumes its second state; and a reference capacitor coupled between ground potential and the switching device at its common pole such that in the first state the switching device decouples the reference capacitor and the noninverting input from the first electrode of the coupling capacitor, whereby substantially no charge is transferred between the reference capacitor and the coupling capacitor, and in the second state the switching device couples the reference capacitor and the noninverting input to the first electrode of the coupling capacitor, whereby charge is transferred between the reference capacitor and the coupling capacitor;

whereby the voltage potential of the electrode is maintained on the reference capacitor and at the noninverting input in response to the passage of the oscillating clock signal, and whereby the voltage potential at the electrode is not maintained on the reference capacitor and at the noninverting input in response to the non-passage of the oscillating clock signal.

8. The active discharge device of claim 7, including:

a pace/sense lead coupled between a pace/sense location and the second electrode of the coupling capacitor;

a housing that contains the active discharge device, the housing having an electrically conductive surface thereon, the electrically conductive surface being coupled to ground potential;

the reference voltage being ground potential.

9. The active discharge device of claim 8, wherein the therapy circuit is a cardiac pacemaker.

10. The active discharge device of claim 7, including:

a bipolar pace/sense lead coupled, using a first electrode of the bipolar pace/sense lead, between a pace/sense location and the second electrode of the coupling capacitor, and coupled using a second electrode of the bipolar pace/sense lead, between the pace/sense location and the reference voltage at the inverting input of the comparator.

11. The active discharge device of claim 10, wherein the therapy circuit comprises a cardiac pacemaker.

12. In an implantable medical device, a method for actively discharging a coupling capacitor after an electrical pulse has been passed through the coupling capacitor from a therapy circuit to an animal tissue, wherein a first electrode of the coupling capacitor is coupled to the therapy circuit within the implantable medical device and wherein a second electrode of the coupling capacitor is coupled to the animal tissue, the method including:

(a) coupling a charge transfer capacitor to a discharge voltage supply so as to transfer charge between the charge transfer capacitor and the discharge voltage supply;

(b) decoupling the charge transfer capacitor from the discharge voltage supply; and (c) coupling, the charge transfer capacitor to the first electrode of the coupling capacitor so as to transfer charge between the charge transfer capacitor and the coupling capacitor, wherein the coupling capacitor is at least partially discharged by the transfer of charge between the charge transfer capacitor and the coupling capacitor.

13. The method of claim 12, including:

(d) decoupling the charge transfer capacitor from the first electrode of the coupling capacitor;

(e) repeating steps (a) through (d) so as to discharge the coupling capacitor until a voltage potential at the first electrode reaches approximately a reference potential.

14. The method of claim 13, including:

(f) stopping the repeating in step (e) when the voltage potential at the first electrode reaches approximately the reference potential;

(g) resuming the repeating in step (e) in response to a trigger signal that is generated by the therapy circuit in response to the passing of the electrical pulse through the coupling capacitor by the therapy circuit.

15. The method of claim 14, including:

(h) repeating the stopping in step (f) and the resuming in step (g).

16. The method of claim 15, wherein the stopping in step (f) is in response to transitioning a comparator output of a comparator from a first output voltage to a second output voltage and wherein the resuming in step (g) is in response to transitioning a trigger signal from the therapy circuit from a first state to a second state.

17. The method of claim 16, wherein the stopping in step (f) is in response to the transitioning of the comparator output from the first output voltage to the second output voltage, the transitioning causing a latching device to be reset and further causing an output of the latching device to assume a disabled state, and wherein the resuming in step (g) is in response to the transitioning of the trigger signal from the first state to the second state, the transitioning causing the latching device to be clocked, causing the latching device to read an enable signal from an input of the latching device, and further causing the output of the latching device to assume an enabled state.

18. The method of claim 17, wherein the repeating in step (e) is in response to passing a clock signal to a control input of a switch that performs the coupling in steps (a) and (c) and the decoupling in steps (b) and (d).

19. The method of claim 18, wherein the stopping in step (f) is in response to stopping the passing of the clock signal to the control input, and the resuming in step (g) is in response to resuming the passing of the clock signal to the control input.

20. The method of claim 19, wherein the stopping of the passing of the clock signal is in response to changing the output of the latching device to the disabled state and wherein the resuming of the passing of the clock signal is in response to changing the output of the latching device to the enabled state.

21. The method of claim 20, wherein the passing of the clock signal is through a gate device, wherein the clock signal is passed through the gate device in response to the changing of the output of the latching device to the enabled state and is not passed in response to the changing of the output of the latching device to the disabled state.

22. The method of claim 16, wherein the stopping in step (f) is in response to the comparator output of the comparator transitioning, the comparator having an inverting input and a non-inverting input, the method including coupling the inverting input of the comparator to the reference potential and repeatedly coupling and then decoupling the non-inverting input to the first electrode of the coupling capacitor.

23. An implantable medical device comprising:

a therapy circuit for providing therapeutic stimulation pulses to body tissue;

a coupling capacitor coupled between the therapy circuit and body tissue; and a discharge circuit comprising:

a source of electrical charge;

a transfer capacitor; and switching means for selectively electrically interconnecting the transfer capacitor between ground and one of said charge source and said coupling capacitor, whereby when connected to the charge source, the transfer capacitor is charged by the charge source and when connected to the coupling capacitor, the transfer capacitor causes charge to be transferred between the transfer capacitor and the coupling capacitor so as to discharge the coupling capacitor.

24. The implantable medical device of claim 23, further comprising means for controlling when the switching means electrically interconnects the transfer capacitor to the charge source and to the coupling capacitor.

* * * * *